United States Patent
Hunt et al.

(10) Patent No.: US 11,275,021 B2
(45) Date of Patent: Mar. 15, 2022

(54) SUBSTANCE TESTING SYSTEM AND METHOD

(71) Applicant: Alcolizer Pty Ltd, Cleveland (AU)

(72) Inventors: Roger Alan Hunt, Cleveland (AU); James John Brown, Cleveland (AU)

(73) Assignee: Alcolizer Pty Ltd., Brisbane (AU)

(*) Notice: Subject to any disclaimer, the term of this patent is extended or adjusted under 35 U.S.C. 154(b) by 0 days.

(21) Appl. No.: 16/330,005

(22) PCT Filed: Sep. 1, 2017

(86) PCT No.: PCT/AU2017/050943
§ 371 (c)(1),
(2) Date: Mar. 1, 2019

(87) PCT Pub. No.: WO2018/039736
PCT Pub. Date: Mar. 8, 2018

(65) Prior Publication Data
US 2019/0204211 A1     Jul. 4, 2019

(30) Foreign Application Priority Data

Sep. 2, 2016  (AU) ................ 2016903515

(51) Int. Cl.
| | | |
|---|---|---|
| *G01N 21/17* | (2006.01) | |
| *G01N 21/84* | (2006.01) | |
| *A61B 5/00* | (2006.01) | |
| *G01N 21/89* | (2006.01) | |

(52) U.S. Cl.
CPC .......... *G01N 21/17* (2013.01); *A61B 5/0095* (2013.01); *G01N 21/8483* (2013.01); *G01N 2021/8908* (2013.01); *G01N 2201/0221* (2013.01)

(58) Field of Classification Search
CPC ............ B01L 3/502715; B01L 3/5023; B01L 3/502707; B01L 3/502723; G01N 21/17; G01N 21/8483; G01N 2021/8908; G01N 2201/0221; A61B 5/0095
USPC ....... 356/432–440; 436/501; 422/69, 50, 55, 422/56, 58, 68.1, 82.05, 99, 104
See application file for complete search history.

(56) References Cited

U.S. PATENT DOCUMENTS

| | | | |
|---|---|---|---|
| 5,397,538 A | 3/1995 | Stark | |
| 9,891,217 B2* | 2/2018 | Petruno | G01N 33/558 |
| 10,049,256 B2* | 8/2018 | Wu | G06K 9/0004 |
| 2003/0119202 A1* | 6/2003 | Kaylor | G01N 21/8483 436/514 |

(Continued)

FOREIGN PATENT DOCUMENTS

| | | |
|---|---|---|
| CN | 201917526 U | 8/2011 |
| EP | 0653625 A1 | 5/1995 |

(Continued)

*Primary Examiner* — Hoa Q Pham
(74) *Attorney, Agent, or Firm* — DeLio Peterson & Curcio LLC; Thomas E. Ciesco (57) ABSTRACT

A substance testing method, a substance testing system, and a sensor module for a portable substance testing system is disclosed. The sensor module includes: a light source, configured to illuminate a lateral flow test strip of the portable substance testing system; a filter, comprising a plurality of apertures, configured to filter out light from the lateral flow test strip; and a sensor, for sensing the filtered light, and providing one or more signals indicative of an output of the test strip.

17 Claims, 6 Drawing Sheets

(56) References Cited

U.S. PATENT DOCUMENTS

| | | | |
|---|---|---|---|
| 2006/0008896 A1 | 1/2006 | Nazareth | |
| 2006/0197955 A1 | 9/2006 | Koike | |
| 2006/0240541 A1* | 10/2006 | Petruno | G01N 21/274 |
| | | | 435/287.2 |
| 2006/0292040 A1 | 12/2006 | Wickstead et al. | |
| 2007/0185679 A1* | 8/2007 | Petruno | G01N 21/6428 |
| | | | 702/117 |
| 2008/0199851 A1* | 8/2008 | Egan | B01L 3/5023 |
| | | | 435/5 |
| 2011/0050407 A1* | 3/2011 | Schoenfeld | A61B 10/0051 |
| | | | 340/426.11 |
| 2013/0066172 A1* | 3/2013 | Kulcke | A61B 5/7239 |
| | | | 600/310 |
| 2013/0310756 A1 | 11/2013 | Whalley | |
| 2015/0301031 A1* | 10/2015 | Zin | G01N 33/48792 |
| | | | 436/164 |
| 2016/0077091 A1 | 3/2016 | Tyrrell | |
| 2016/0209410 A1* | 7/2016 | Fukushima | G01N 33/54386 |
| 2018/0264464 A1* | 9/2018 | Greef | B01L 3/502715 |
| 2018/0349673 A1* | 12/2018 | Lin | G02B 27/46 |
| 2019/0111426 A1* | 4/2019 | Mai | A61B 5/15 |
| 2019/0183418 A1* | 6/2019 | Hunt | A61B 5/742 |

FOREIGN PATENT DOCUMENTS

| | | | |
|---|---|---|---|
| EP | 1107316 A2 * | 1/2001 | |
| EP | 1564546 A1 | 8/2005 | |
| WO | 2006096210 A2 | 4/2006 | |

\* cited by examiner

SUBSTANCE TESTING SYSTEM AND METHOD

TECHNICAL FIELD

The present invention relates to a testing system, for testing the presence of substances, such as drugs, in a person.

BACKGROUND ART

Many substances, such as alcohol or drugs, are well known and may impair human performance. Random breath testing is a known way testing for the presence of alcohol in drivers, where sampled breath is monitored on a roadside.

In recent times, random drug testing has also become more common. Roadside drug testing typically involves obtaining a saliva sample of a driver using a swab, and analyzing the sample using test strips. Similar testing may also be often performed in workplaces.

A problem with such drug testing of the prior art is that it is not as straightforward as conducting an alcohol RBT, as the test strips must be visually analysed by a person. In particular, tests may be performed in incorrect conditions, rendering the result invalid, and even when a test is otherwise performed correctly, the output of the test strips may be incorrectly interpreted.

As such, there is a need for an improved testing system, for testing the presence of substances, such as drugs, in a person.

It will be clearly understood that, if a prior art publication is referred to herein, this reference does not constitute an admission that the publication forms part of the common general knowledge in the art in Australia or in any other country.

SUMMARY OF INVENTION

The present invention is directed to substance testing systems, which may at least partially overcome at least one of the abovementioned disadvantages or provide the consumer with a useful or commercial choice.

With the foregoing in view, the present invention in one form, resides broadly in a sensor module for a portable substance testing system, the sensor module including:
a light source, configured to illuminate a lateral flow test strip of the portable substance testing system;
a filter, comprising a plurality of apertures, configured to filter out light from the lateral flow test strip; and
a sensor, for sensing the filtered light, and providing one or more signals indicative of an output of the test strip.

Preferably, the portable substance testing system is handheld.

Preferably, the substance is a mind-altering substance.

Preferably, the apertures are elongate.

The elongate apertures may be configured to reduce interference along a length of the strip. The elongate apertures may be configured to reduce noise across a width of the strip.

The elongate apertures may be rectangular in cross section. The apertures may have a narrow edge along a length of the test strip, to provide a narrow range along a length of the test strip. The apertures may have a long edge across a width of the test strip, to provide a broad range across a width of the test strip.

The apertures may be about 1.2 mm deep. The apertures may be about 100 um by about 600 um in cross section. The apertures may be arranged in rows, corresponding to rows of the sensor.

Preferably, the filter comprises a plurality of layers, wherein the elongate apertures are formed from apertures in each of the layers. Suitably, the layers are formed of opaque material. The opaque material may comprise stainless steel.

The layers may each be about 200 um thick. The filter may comprise about 6 layers. The filter may be about 1.2 mm thick. The apertures may be about 100 um in diameter.

Light source may be configured to illuminate the test strip such that the light to be filtered is reflected from a surface of the test strip.

Preferably, the sensor module is configured to receive a sample cartridge, including the lateral flow test strip. Suitably, the sample cartridge includes a plurality of lateral flow test strips. The lateral flow test strips may be configured to react to the presence of different substances.

The cartridge may include alignment members, to ensure that the cartridge is received by the sensor module in a correct position.

The sensor module may be configured to read data from the cartridge. The data may be read from an electronic memory of the cartridge. The data may include a cartridge expiry date, a cartridge type, operational limits of the cartridge, such as altitude or temperature, and/or manufacturing batch parameters Preferably, the light source comprises a plurality of light emitting diodes (LEDs). The light source may be configured to illuminate the test strips in a uniform, or near uniform manner.

Preferably, the LEDs are configured to emit light at multiple wavelengths. Suitably, a first set of the plurality of LEDs is configured to emit light at one wavelength, and a second set. Alternatively, the LEDs may be configurable to emit light at different wavelengths.

Preferably, when in use, test areas (or stripes) of the test strips are not visible to the user.

In another form, the invention resides broadly in a substance testing system comprising:
a lateral flow test strip, configured to detect the presence of a substance in a sample;
a light source, configured to illuminate the lateral flow test strip;
a filter, comprising a plurality of apertures, configured to filter out light from the lateral flow test strip; and
a sensor, for sensing the filtered light, and providing one or more signals indicative of an output of the test strip.

The substance testing system may include a display, for displaying data indicative of an output of the test strip.

In yet another form, the invention resides broadly in a substance testing method including:
illuminating, using a light source, a lateral flow test strip of a portable substance testing system;
filtering, using a filter comprising a plurality of apertures, light from the lateral flow test strip;
sensing, using a sensor, the filtered light, and
providing one or more signals indicative of an output of the test strip.

Any of the features described herein can be combined in any combination with any one or more of the other features described herein within the scope of the invention.

The reference to any prior art in this specification is not, and should not be taken as an acknowledgement or any form of suggestion that the prior art forms part of the common general knowledge.

BRIEF DESCRIPTION OF DRAWINGS

Various embodiments of the invention will be described with reference to the following drawings, in which.

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way.

DESCRIPTION OF EMBODIMENTS

Figure 1:
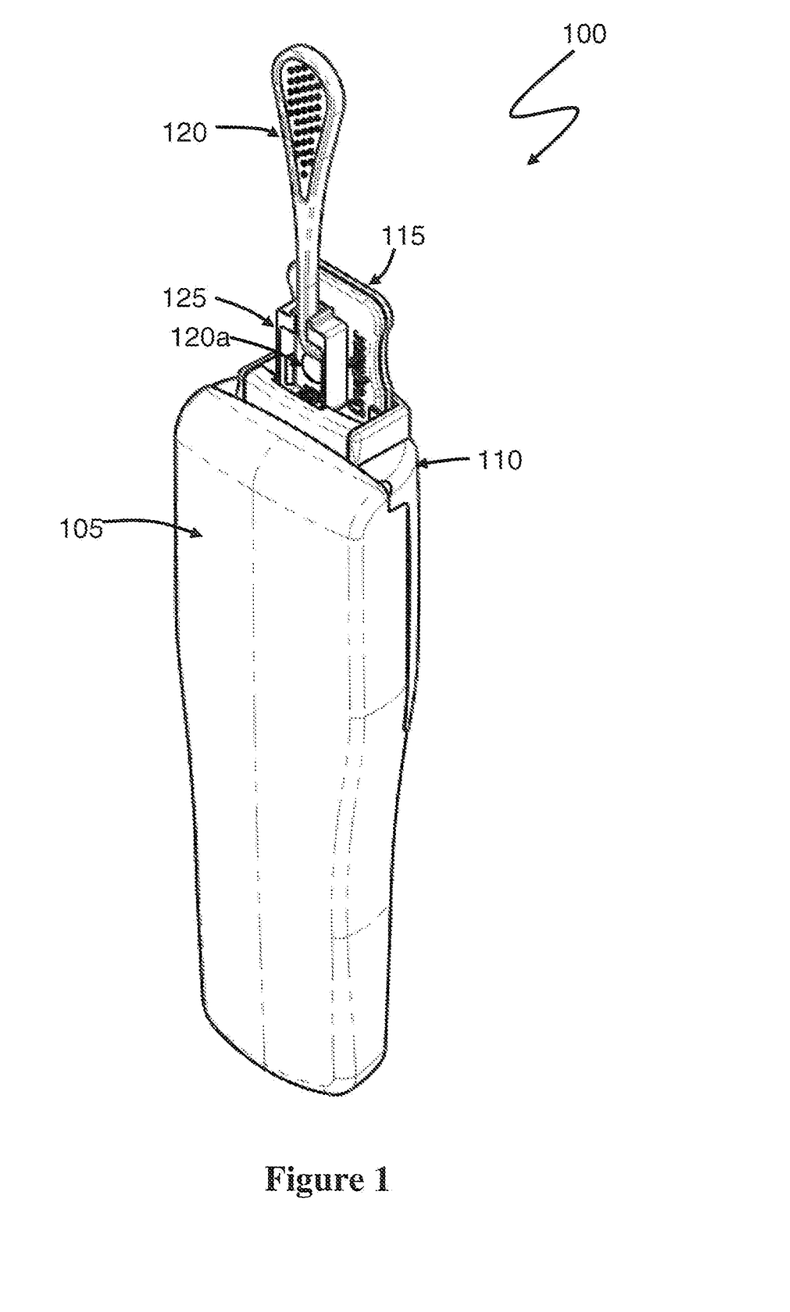
FIG. 1 illustrates a substance testing unit, according to an embodiment of the present invention.

FIG. 1 illustrates a substance testing unit 100, according to an embodiment of the present invention. The substance testing unit 100 is configured to provide portable substance testing, such as drug or alcohol testing, on persons, such as operators of vehicles and workers. As described in further detail below, testing unit 100 is automatic, which provides increased consistency between tests as it removes any human judgement from the assessment process. Furthermore, the testing unit is simple and inexpensive to manufacture, and does not require any complex lenses or optics, which are also prone to damage.

The substance testing unit 100 comprises a body 105, a sensor module 110 coupled to the body 105, a substance sample cartridge 115 coupled to the sensor module 110, and a swab 120 coupled to the substance sample cartridge 115.

A saliva sample is provided to the swab 120, which is coupled to the substance sample cartridge 115 by inserting a sample end 120a of the swab 120 into a sample dock 125 of the cartridge 115.

As described in further detail below, the cartridge 115 includes lateral flow test strips, for sensing substances in the saliva sample, and the sensor module 110 is configured to automatically read a test result of the lateral flow test strips. This removes any human judgement when tests are analysed, which increases reliability and consistency of results.

The cartridge 115 is single use, and thus disposable. However, as outlined below, a memory is provided in the cartridge, for storing information relating to the cartridge.

Finally, while not illustrated, the skilled addressee will readily appreciate that the body 105 may include an interface, such as buttons and a display screen, a portable printer, or a data interface enabling a user to interact with the substance testing unit 100, and read results therefrom, either directly or using another device.

Figure 2:
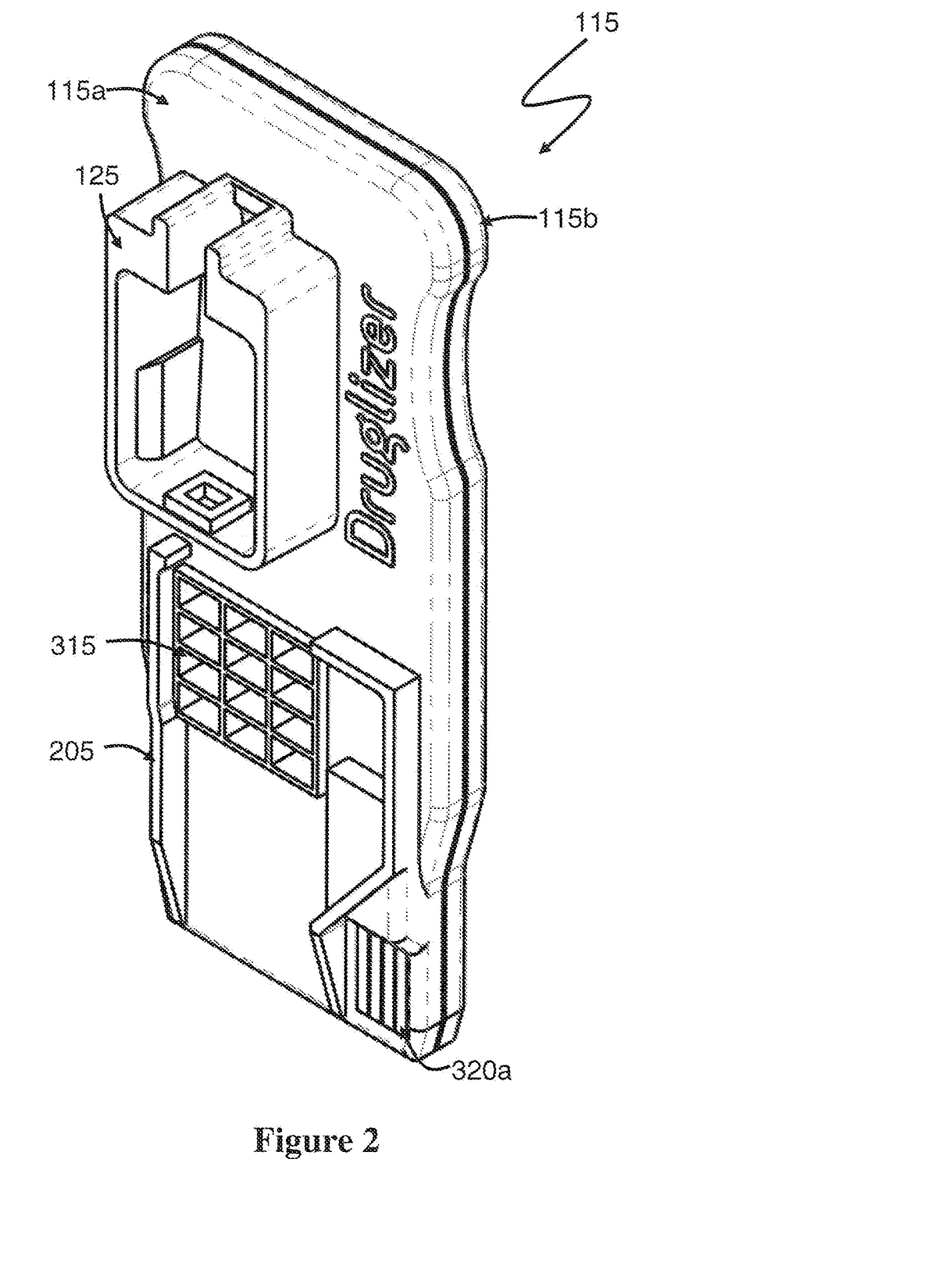
FIG. 2 illustrates a perspective view of a cartridge of the substance testing unit of FIG. 1, according to an embodiment of the present invention.
Figure 3:
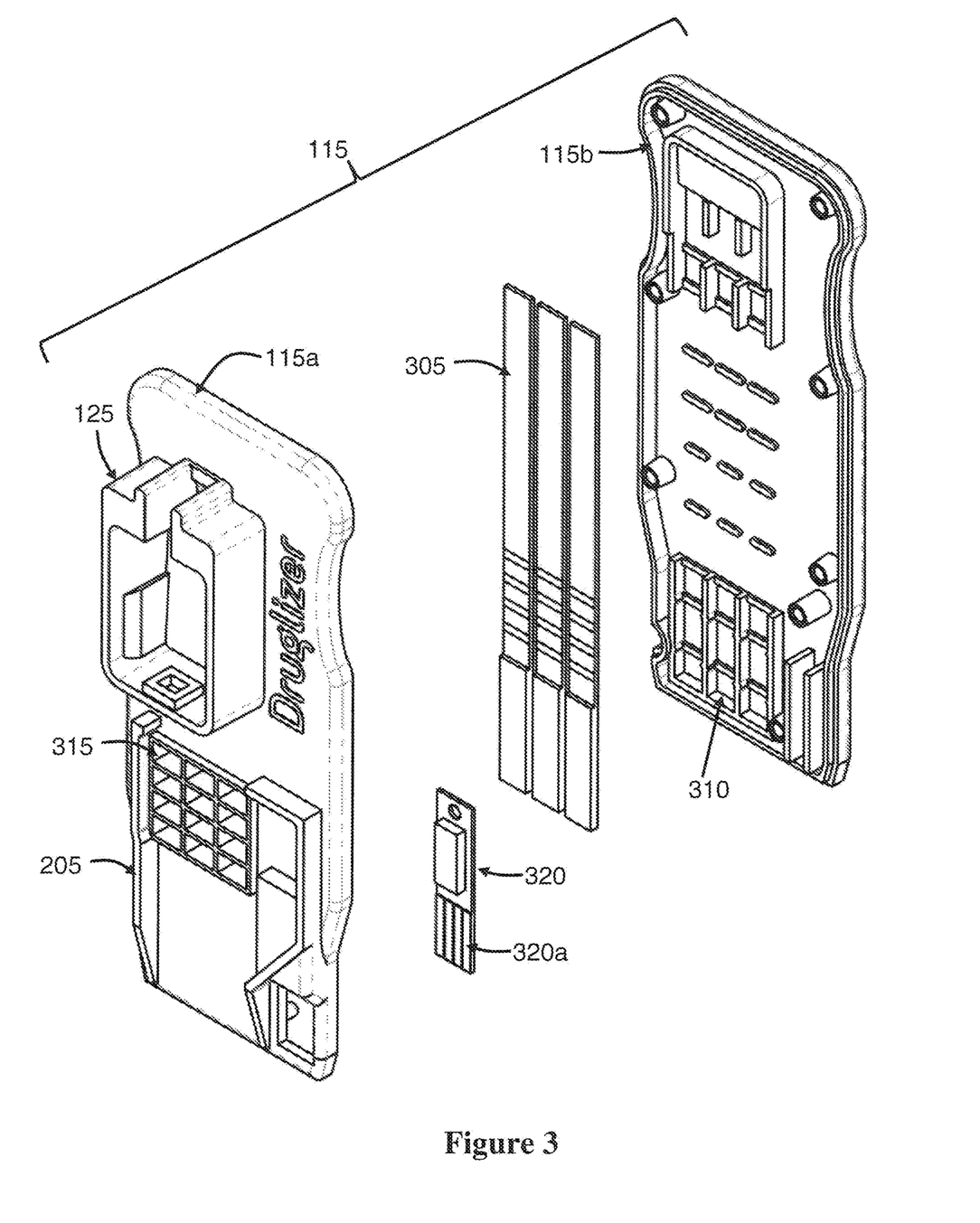
FIG. 3 illustrates an exploded view of the cartridge of FIG. 2.

FIG. 2 illustrates a perspective view of the cartridge 115, according to an embodiment of the present invention. FIG. 3 illustrates an exploded view of the cartridge 115.

A plurality of lateral flow test strips 305 are received between a front side 115a and a rear side 115b of the cartridge 115. A upper end of the lateral flow test strips 305 are received in a portion of the cartridge 115 adjacent to the sample dock 125, and the sample dock 125 is configured such that the saliva is transferred to the upper end of the test strips 305. In particular, a rear surface of the sample dock 125 comprises the upper ends of the test strips 305 when the cartridge 115 is assembled.

The rear side 115b of the cartridge 115 includes a plurality of retaining channels 310, which are configured to retain the test strips 305. In particular, the retaining channels 310 include sidewalls, which prevent lateral movement of the test strips 305, and ridges, which clamp lower ends of the test strips together with a rear surface of the front side 115a. Together, the sidewalls and ridges prevent movement of the test strips 305 relative to the cartridge.

The front side 115a of the cartridge 115 includes a plurality of test windows 315, adjacent to test areas (or stripes) of the test strips. The test windows 315, described in further detail below, enable the sensor module 110 to read a result of the test strips. The skilled addressee will, however, readily appreciate that an open area surrounding the test areas of the test strips may be provided instead of individual windows. In particular, a row of test windows may be replaced by a single elongate opening.

In some embodiments, the cartridge includes further shielding, to prevent ambient light ingress. This is particularly advantageous when used in daylight as it prevents ambient light from influencing sensor data. In one particular embodiment, wings may extend from either side of the sample dock 125 to shield light from extending into the test areas of the test strips from above.

The cartridge 115 includes alignment members 205 to ensure that the cartridge 115 is received by the sensor module in a correct position. The alignment members 205 may act as guide members, as the cartridge 115 is inserted, and provide height alignment of the cartridge.

Finally, the cartridge 115 includes an electronic memory module 320, for storing data relating to the cartridge 115. Examples of data stored on the electronic memory includes a cartridge expiry date, a cartridge type, operational limits of the cartridge, such as altitude or temperature, and/or manufacturing batch parameters.

In use, the data from the electronic memory module 320 is read by the sensor module 110, using interface pins 320a of the memory module 320, to provide instruction to the user, prevent or warn against the use of expired cartridges, identify a cartridge type, or compensate test data for improved accuracy.

Figure 4:
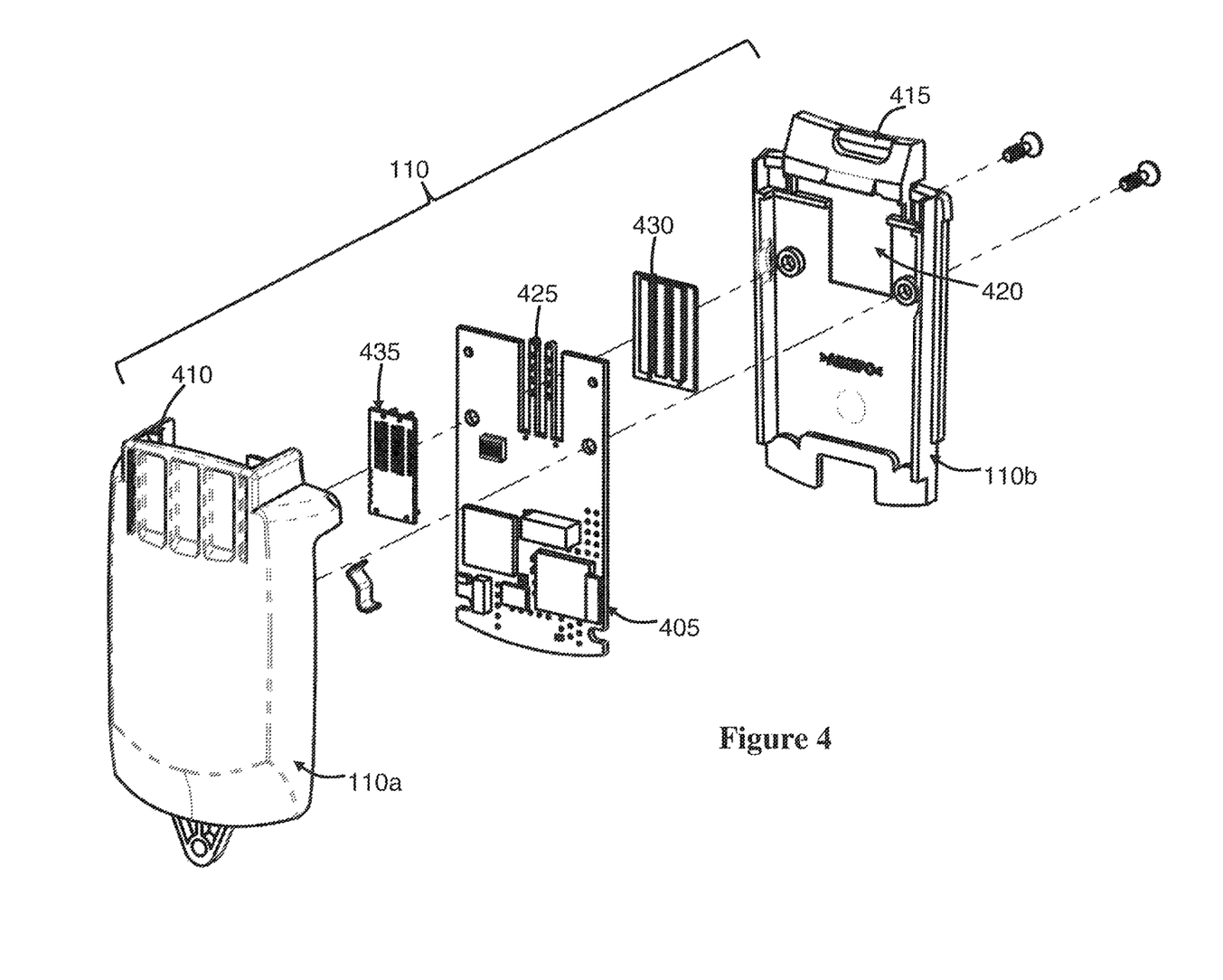
FIG. 4 illustrates an exploded view of the sensor module of the substance testing unit of FIG. 1, according to an embodiment of the present invention.

FIG. 4 illustrates an exploded view of the sensor module 110, according to an embodiment of the present invention.

The sensor module 110 includes a front side 110a and a rear side 110b, which together form a housing to store a printed circuit board 405 and circuitry to analysing a sample using the cartridge 115.

The front side 110a includes a channel 410 for receiving the cartridge 115, and the rear side 110b includes a recess 415 for receiving the sample dock 125 of the cartridge 115.

The rear side further includes an opening 420, which is configured to provide clearance around the sensor 430.

As described in further detail below, a light source in the form of a plurality of light emitting diodes (LEDs) 425 is configured to illuminate the test strips through the test windows 310, upon which reflected light filtered by a filter 435, prior to being sensed by sensors 430, to determine a test result.

Figure 5:
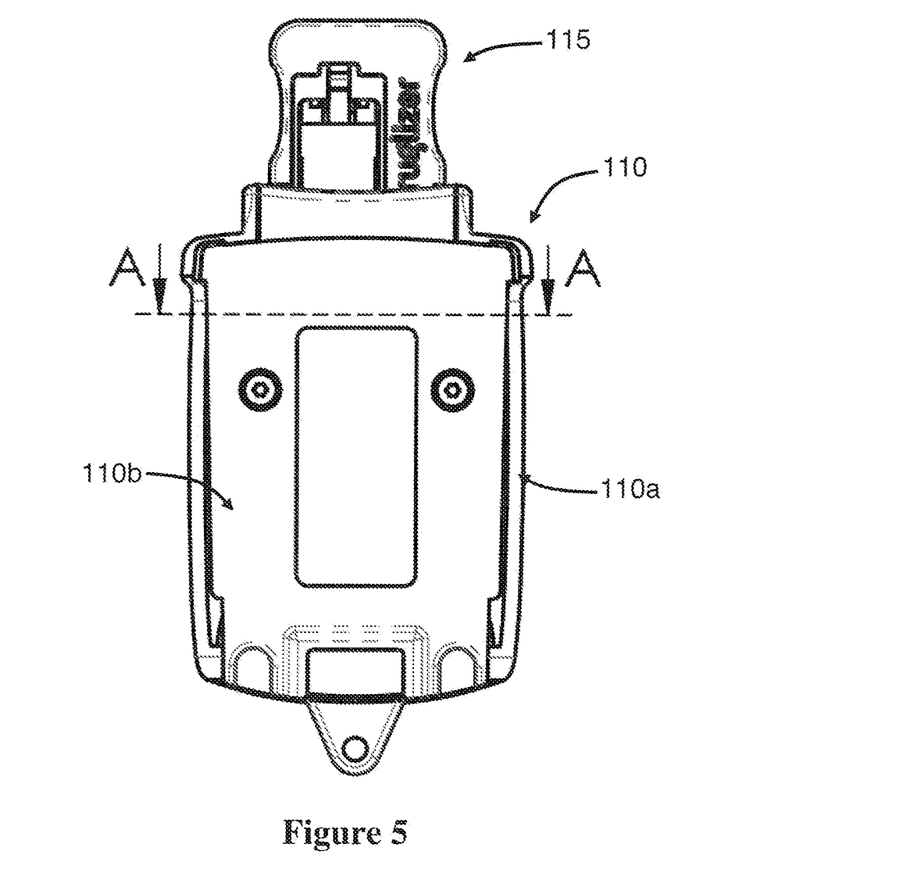
FIG. 5 illustrates a rear view of the sensor module of FIG. 4.
Figure 6A:
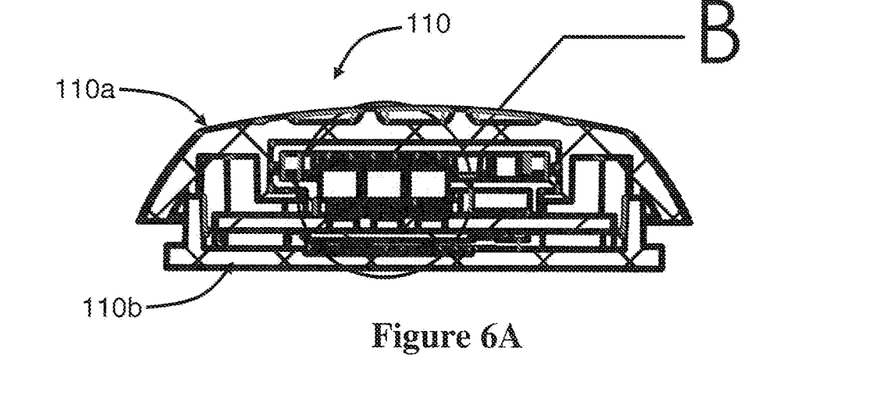
FIG. 6A illustrates a cross sectional view of the sensor module of FIG. 4 along A-A.
Figure 6B:
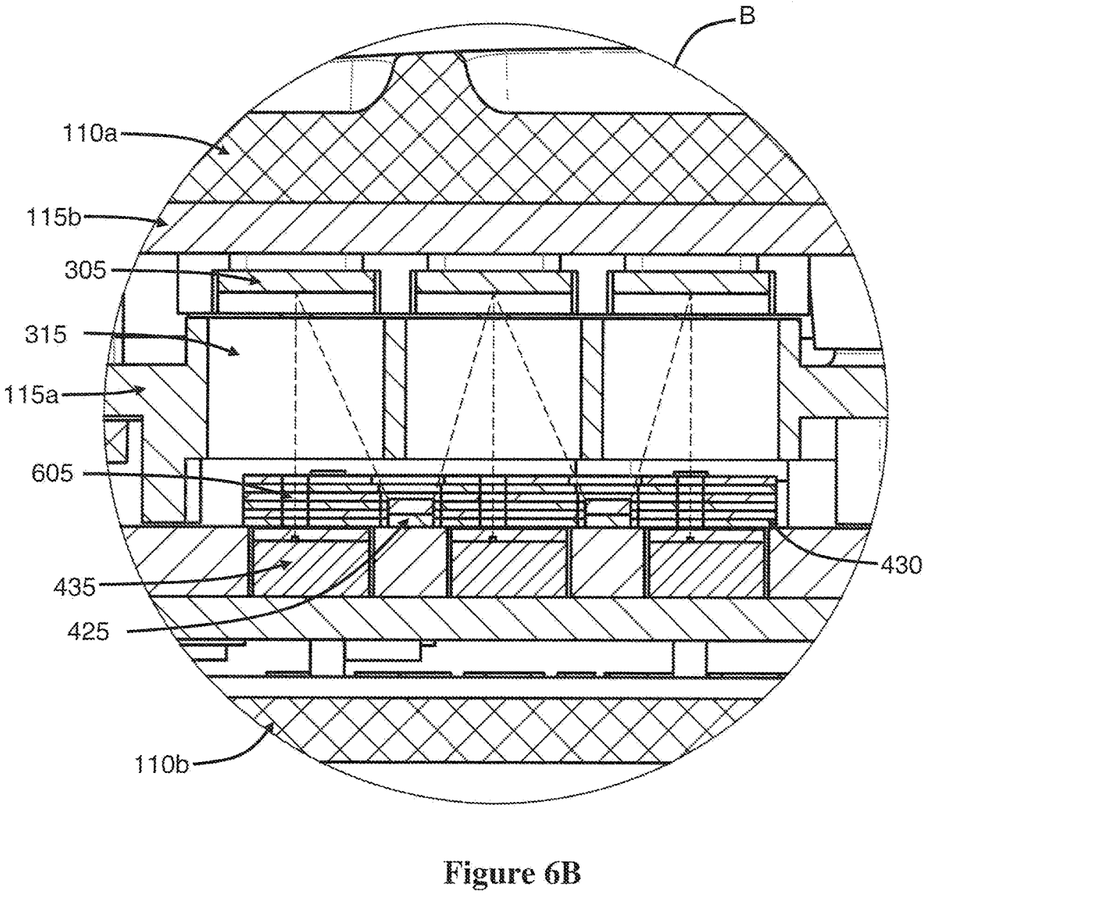
FIG. 6B illustrates an enlarged view of a portion of the cross section view of FIG. 6A.

FIG. 5 illustrates a rear view of the sensor module 110. FIG. 6A illustrates a cross sectional view of the sensor module 110 along A-A and FIG. 6B illustrates an enlarged view of area B of the sensor module 110.

As best illustrated with reference to FIG. 6B, light is emitted from the LEDs 425 and illuminates the test strips 305. In particular, two rows of LEDs are provided, positioned between and along an axis of the test strips 305, to illuminate the three test strips 305 through the windows 310.

The filter 430 comprises several layers of stainless steel each with apertures that are aligned to form elongate apertures 605 in the filter 430, that are perpendicular to a surface of the test strips 305. As the light emitted from the LEDs 425 is diffused, and further diffused when reflected from the test strip 425, the filter enables a sharp image of the test strip to be received at the sensor 435, without the use of lenses or complex optics to focus the light onto the sensor 435.

The layers of stainless steel comprise about six (6) layers, each of which is about 200 um thick, thus forming a stack which is about 1.2 mm high. Each layer is laser cut to form apertures that are about 100 um by about 600 um in cross section. The apertures are arranged in rows, corresponding to rows of the sensor 435.

By providing apertures that are rectangular in cross section, and with a narrow edge along a length of the test strip, the directional filter is provided that has a relatively narrow range along a length of the strip, while having a broad range across a width of the test strip. Such arrangement is good at detecting stripes on the test strip, as interference along a length of the strip is reduced, while noise across a width of the strip is reduced.

By using the layers of stainless steel, very small apertures can be relatively simply manufactured, with the level of detail required to ensure the functionality of the filter 430. In other words, the filter 430 provides a good balance between manufacturability (where it is difficult to cut small apertures into thick metal) and having sufficient accuracy to restrict the "viewing angle" of the sensor to provide sufficient discrimination of the incoming light.

The sensor 435 comprises an array of photosensitive elements arranged in a line known as a linear detector (also line-camera or line-scanner), and a separate linear detector is used for each lateral flow strip 305. This enables different tests to be performed independently in relation to each of the test strips 305, for example to test for different substances.

Once the signal is received at the sensor 430, one or more algorithms and/or digital filters may be applied to the signal of the sensor to ultimately determine the presence of one or more substances in the saliva sample.

According to certain embodiments, the LEDs 435 may comprise a plurality of LEDs having different wavelengths. As an illustrative example, by using RGB (red-green-blue) tri-colour LEDs, multiple wavelengths (frequencies) can be assessed simultaneously. In some cases, LEDs may be chosen that has a wavelength particularly suited to the type of cartridge, and thus multispectral illumination allows the device to vary its response to best suit the type of lateral flow assay used.

According to certain embodiments, the sensor module 110 includes an orientation sensor, for monitoring the orientation of the test during operation. This is particularly advantageous, as lateral flow tests are generally subject to the effects of gravity, and a warning may be provided to the user if the unit 100 is held in an inappropriate position. Data from the orientation sensor may even prevent a sample from being read, or invalidate a result of the unit 100.

Advantageously, the unit 100 is easy to use, and does not require any visual interpretation by the user. Furthermore, by using the filter, as described above, between the test strips and the sensor, a simple, inexpensive and robust means of providing high contrast (non-blurry) data of the test strips is provided. This is very useful as the unit is portable and handheld, and thus exposed to being knocked and dropped.

While above has been described with reference to saliva, the skilled addressee will readily appreciate that the system may be adapted to suit urine, or other types of samples (analytes).

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

The invention claimed is:

1. A sensor module for a portable, substance testing system, the sensor module including:
   a light source to illuminate a lateral flow test strip of the portable substance testing system;
   a filter, comprising a plurality of apertures to filter out light from the lateral flow test strip; and
   a sensor sensing the filtered light and providing one or more signals indicative of an output of the test strip, wherein
   the substance testing system is for detecting the presence of a substance in a sample and the light source illuminates the test strip such that the light to be filtered is reflected from a surface of the test strip,
   the light only travels through the filter after being reflected, and
   the filter comprises a plurality of layers formed of opaque material, wherein the apertures are formed from apertures in each of the layers, and the apertures are aligned to form elongated apertures.

2. The sensor module of claim 1, wherein the portable substance testing system is handheld, and/or wherein the substance is a mind altering substance.

3. The sensor module of claim 1, wherein the elongate apertures reduce interference along a length of the strip;
   are rectangular in cross section;
   have a narrow edge along a length of the test strip, to provide a narrow range along a length of the test strip; and/or,
   have a long edge across a width of the test strip, to provide a broad range across a width of the test strip.

4. The sensor module of claim 1, wherein the apertures are:

about 1.2 mm deep;
about 100 um by about 600 um in cross section; and/or,
arranged in rows, corresponding to rows of the sensor.

5. The sensor module of claim 1, wherein:
the layers are of material comprising stainless steel; and/or,
the layers are each about 200 um thick; and/or
the filter comprises about 6 layers, and the filter is about 1.2 mm thick.

6. The sensor module of claim 1, wherein the apertures are about 100 um in diameter.

7. The sensor module of claim 1, wherein the sensor module receives a sample cartridge, including the lateral flow test strip.

8. The sensor module of claim 7, wherein the sample cartridge includes;
a plurality of lateral flow test strips, and the lateral flow test strips react to the presence of different substances; and/or
alignment members, to ensure that the sample cartridge is received by the sensor module in a correct position.

9. The sensor module of claim 7, wherein the sensor module reads data from the sample cartridge.

10. The sensor module of claim 9, wherein the data is read from an electronic memory of the cartridge.

11. The sensor module of claim 10, wherein the data includes a cartridge expiry date, a cartridge type, altitude and/or temperature operational limits of the cartridge, and/or manufacturing batch parameters.

12. The sensor module of claim 1, wherein the light source comprises a plurality of light emitting diodes (LEDs).

13. The sensor module of claim 12, wherein the LEDs emit light at multiple wavelengths, and/or a first set of the plurality of LEDs is configured to emit light at one wavelength, and a second set of LEDs is configured to emit light at another wavelength.

14. The sensor module of claim 1, wherein, in use, test areas of the test strips are not visible to the user.

15. A substance testing system comprising:
a lateral flow test strip, configured to detect the presence of a substance in a sample;
a light source to illuminate the lateral flow test strip;
a filter, comprising a plurality of apertures to filter out light from the lateral flow test strip; and
a sensor, for sensing the filtered light reflected from a surface of the test strip, and providing one or more signals indicative of an output of the test strip, wherein
the light only travels through the filter after being reflected,
the filter comprises a plurality of layers formed from opaque material, wherein the apertures are formed from apertures in each of the layers, and
the apertures are aligned to form elongated apertures.

16. The system of claim 15 including a display, for displaying data indicative of an output of the test strip.

17. A substance testing method including:
illuminating, using a light source, a lateral flow test strip of a portable substance testing system for detecting the presence of a substance in a sample;
filtering, using a filter comprising a plurality of apertures, light from the lateral flow test strip;
sensing, using a sensor, the filtered light, and
providing one or more signals indicative of an output of the test strip, wherein the light source illuminates the test strip such that the light to be filtered is reflected from a surface of the test strip,
the light only travels through the filter after being reflected and
the filter comprises a plurality of layers formed from opaque material, wherein the apertures are formed from apertures in each of the layers, and the apertures are aligned to form elongated apertures.

* * * * *